(12) United States Patent
Nishihara et al.

(10) Patent No.: US 8,088,082 B2
(45) Date of Patent: Jan. 3, 2012

(54) FETAL MOVEMENT MONITORING SYSTEM AND FETAL MOVEMENT INFORMATION COLLECTING DEVICE

(75) Inventors: Kyoko Nishihara, Fuchu (JP); Shigeko Horiuchi, Tsuruoka (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 55 days.

(21) Appl. No.: 11/883,895

(22) PCT Filed: Feb. 7, 2006

(86) PCT No.: PCT/JP2006/302045
§ 371 (c)(1),
(2), (4) Date: Aug. 6, 2007

(87) PCT Pub. No.: WO2006/082977
PCT Pub. Date: Aug. 10, 2006

(65) Prior Publication Data
US 2008/0154155 A1   Jun. 26, 2008

(30) Foreign Application Priority Data
Feb. 7, 2005 (JP) .................................. 2005-030789

(51) Int. Cl.
*A61B 5/103* (2006.01)
(52) U.S. Cl. ..................... 600/595; 600/588; 600/549
(58) Field of Classification Search .......... 600/595, 600/588, 549
See application file for complete search history.

(56) References Cited

U.S. PATENT DOCUMENTS

| | | | | |
|---|---|---|---|---|
| 4,781,200 A | * | 11/1988 | Baker | 600/483 |
| 5,817,035 A | * | 10/1998 | Sullivan | 600/588 |
| 6,045,500 A | * | 4/2000 | Bieniarz | 600/300 |
| 2001/0014776 A1 | * | 8/2001 | Oriol et al. | 600/511 |

FOREIGN PATENT DOCUMENTS

| | | |
|---|---|---|
| JP | 10-511015 | 10/1998 |
| JP | 11-089832 | 4/1999 |
| JP | 2002-065640 | 3/2002 |
| WO | WO 03/055386 | 7/2003 |

OTHER PUBLICATIONS

Sanfujinkairyo, 1999 Supplement. (vol. 78), pp. 224-228, "Fetal Asphyxia and Its Countermeasure" by Hideki Kawaguchi, et al. published in Japan in 1999.

* cited by examiner

*Primary Examiner* — Max Hindenburg
*Assistant Examiner* — Renee Danega
(74) *Attorney, Agent, or Firm* — DLA Piper LLP (US)

(57) ABSTRACT

The present invention provides a fetal movement monitoring system and a fetal movement information collecting device which are simply usable at home to collect and analyze correctly detail information about fetal movements over a long time. The fetal movement monitoring system includes a fetal movement information collecting device 21 and an analyzing device 40, wherein the fetal movement information collecting device 21 includes a fetal movement sensor 22 for detecting the movement of a fetus in the uterus of the mother's body, a timer 25 for outputting time information, a memory 26, and a storage control means 24 which receives the output signal from the fetal movement sensor 22 and stores, in the memory 26, waveform information of the output signal obtained for a period from the time when the output signal reaches a level to exceed a predetermined threshold value until a predetermined time elapses along with time information at the time; and the analyzing device 40 which bases on the waveform information and the time information stored in the memory 26 to reproduce signal waveform, to determine fetal movement type, and to produce fetal movement occurrence pattern, and bases on the occurrence pattern to determine whether a fetus is smoothly growing or not, and displays the determination result on a display 42.

1 Claim, 13 Drawing Sheets

FIG.10

| | 26 |
|---|---|
| TD(1)=k1*Δt | H(1)={X(k1)〜X(k1+n)} |
| TD(2)=k2*Δt | H(2)={X(k2)〜X(k2+n)} |
| TD(3)=k3*Δt | H(3)={X(k3)〜X(k3+n)} |
| --- | --- |
| TD(i)=ki*Δt | H(i)={X(ki)〜X(ki+n)} |

FETAL MOVEMENT MONITORING SYSTEM AND FETAL MOVEMENT INFORMATION COLLECTING DEVICE

TECHNICAL FIELD

The present invention relates to a fetal movement monitoring system for monitoring fetal movements inside a pregnant mother's body, and a fetal movement information collecting device which is able to correctly grasp whether a fetus is growing smoothly and is useful for early detecting the risk of death of a fetus in the uterus.

BACKGROUND ART

Up to now, methods and devices for detecting fetal movement frequencies are known which detect the number of fetal movements in a fixed time period in order to grasp whether a fetus in the uterus of the mother's body is growing smoothly.

As such methods and devices for detecting fetal movement frequencies, various kinds of methods and devices have been proposed and implemented which are configured so that the mother pushes a button when feeling a fetal movement or so that a fetal movement sensor for detecting fetal movements is attached on the mother's abdomen in order to determine whether there is a fetal movement on the basis of the output signal from the fetal movement sensor.

For example, in Japanese Unexamined Patent Publication No. 11-89832 (Patent Document 1), a fetal movement measuring instrument is disclosed which is configured so that fetal movements are detected using a thin-film piezoelectric sensor, and it is determined that the fetus is healthy if a predetermined number (10) or more of fetal movements are detected within a fixed period of time (two hours) or it is determined that the fetus is in a dangerous condition if the number of fetal movements in a fixed period of time (8 hours) is less than a predetermined number (10).

However, there are differences among fetuses, and fetal movements include those which occur two or more times in a fixed cycle such as "hiccups", those which occurs singly such as "kicks" or "rolls", and the like, so that detecting only fetal movement frequencies as described above is not sufficient for determining the state of health of the fetus.

Furthermore, no movement a fetus gives in a fixed period of time can not necessarily decide that the fetus is in a dangerous condition. For example, "Hideki Kawaguchi, et. al., "Fetal Asphyxia and Its Countermeasure", Sanfujinkairyo (in Japanese), 1999 Supplement. (Vol. 78), pp. 224-228" (Non-patent Document 1) shows data indicating that a healthy fetus gave continuously no movement for a time as long as 75 minutes.

In addition, high sensitivity employed for detecting movements of a fetus in the uterus of the mother's body by signals from the mother's abdomen, catches a signal from the mother by her movement such as breath to count as one component of fetal movement, thereby to count a number beyond real fetal movements, resulting in a risk of missing that the fetus has a reduced number in fetal movement.

Patent Document 1: Japanese Unexamined Patent Publication No. 11-89832

Non-patent Document 1: Hideki Kawaguchi, et. al., "Fetal Asphyxia and Its Countermeasure", Sanfujinkairyo (in Japanese), 1999 Supplement. (Vol. 78), pp. 224-228

DISCLOSURE OF THE INVENTION

Problems to be solved by the Invention

The Patent Document 1 describes that the components of breath of the mother is subtracted from the output of the fetal movement sensor by inverted filtration based on a multidimensional autoregressive (AR) model. However, the AR model is effective on a regular signal, but is not able to address movements such as breaths of the mother which vary to a large degree depending on the physical condition and/or mental state of the mother or whether the mother is sleeping or awake, and may therefore make an erroneous determination due to any movement of the mother's body.

Such a method of grasping the state of health of a fetus by only fetal movement frequencies is not able to address individual fetuses, and may give the contrary effect. Thus, it is necessary to determine the state of health of a fetus on the basis of more detail information related to fetal movements.

In order to obtain more detail information related to fetal movements, a system can be considered which continuously collects the output signal of a sensor for detecting fetal movements over a long time, and bases on the collected data to determine the state of health of a fetus. However, such a system needs a significantly large capacity memory for storing continuous data over a long time, so that even if the system is applicable to a pregnant woman in a hospital, it is difficult to realize as a system which can be personally used at home.

Furthermore, methods of extracting and canceling components such as movements of the mother's body included in the output signal of a sensor for detecting fetal movements are lacking in reliability, and have a risk of inviting error to delay the detection of an abnormal state of a fetus.

In hospitals, the image of a fetus in the uterus of the mother's body is generally monitored by an ultrasonic wave echo device. But, because this type of device is a so-called active sensor type which applies an ultrasonic wave to a fetus in the uterus of the mother's body and receives its reflected wave, it is undesirable to use this type of device for monitoring fetal movements over a long time in consideration of an influence to the fetus. Furthermore, there is a problem that an ultrasonic wave echo device is configured to be used by a specialist such as a doctor or midwife, and can not be used easily by a pregnant woman herself at home.

It is therefore an object of the present invention to provide a fetal movement monitoring system and a fetal movement information collecting device which may be used in the fetal movement monitoring system, which are proposed to solve the problems of the prior art described above and are able to be used easily at home and collect and analyze correctly detail information about fetal movements over a long time.

Means for solving the Problems

In order to achieve the above object, a fetal movement monitoring system as claimed in claim 1 of the present invention comprises: a passive fetal movement sensor which is placed on the abdomen of a mother to detect the movement of a fetus in the uterus of the mother's body; a timer for outputting time information; a storage medium for storing information; a storage control means which receives the output signal from the fetal movement sensor and stores waveform information of the output signal obtained for a period from the time when the output signal reaches a level to exceed a predetermined threshold value until a predetermined period of time along with time information corresponding to the output signal; and an analyzing device which bases on waveform information and time information stored in the storage control means to analyze fetal movements and outputs the analysis result.

The fetal movement monitoring system as claimed in claim 2 of the present invention is characterized in that the analyzing device comprises: a display; and a signal waveform reproducing means which bases on waveform information and time information stored in the storage medium to reproduce a signal waveform which is continuous during a predetermined period of time, and displays the reproduced signal waveform on the display.

The fetal movement monitoring system as claimed in claim 3 of the present invention is characterized in that the analyzing device comprises a fetal movement type determining means which bases on waveform information of the output signal from the fetal movement sensor stored in the storage medium to determine fetal movement type.

The program for fetal movement monitoring as claimed in claim 4 of the present invention comprises: a first step of receiving fetal movement waveform information corresponding to the output signal of a passive fetal movement sensor which is placed on the abdomen of a mother and detects the movement of a fetus in the uterus of the mother's body and receiving time information corresponding to the output signal; a second step of displaying the received fetal movement waveform information and time information on a display; a third step of comparing fetal movement patterns indicating fetal movement types stored in advance with waveform information in a predetermined period of time of the received fetal movement waveform information to determine fetal movement types in the period; and a fourth step of comparing reference patterns, which are criteria for determining the state of health of a fetus and have been stored in advance in correspondence with the number of days in pregnancy, with the received fetal movement waveform information and time information to determine the state of health of the fetus.

The fetal movement monitoring system as claimed in claim 5 of the present invention is characterized in that the fetal movement type determining means obtains a spectral distribution of waveform information of the output signal from the fetal movement sensor and compares the spectral distribution with reference spectral distributions of fetal movements to determine a fetal movement.

The fetal movement monitoring system as claimed in claim 6 of the present invention is characterized in that the analyzing device comprises: an occurrence pattern producing means which bases on the result of determination of the fetal movement type determining means to produce occurrence patterns of fetal movement types in a fixed period of time; and a determining means which stores in advance reference patterns which are criteria for determining the state of health of a fetus and compares occurrence patterns produced by the occurrence pattern producing means with the reference patterns to determine the state of health of a fetus.

The fetal movement monitoring system as claimed in claim 7 of the present invention is characterized in that the fetal movement monitoring system further comprises a mother's movement sensor to detect biological information of a mother's body; the storage control means is configured so as to store, in the storage medium, waveform information of signals outputted from the mother's movement sensor for a period from the time when the output signal from the fetal movement sensor reaches a level to exceed the threshold value until the predetermined period of time elapses along with waveform information of the output signal from the fetal movement sensor, and the analyzing device comprises a fetal movement information extracting means for extracting information which depends on only fetal movements, which have not influenced by the movement of the mother's body, from information stored in the storage medium; and analyzes the information extracted by the fetal movement information extracting means.

The fetal movement information collecting device as claimed in claim 8 of the present invention comprises: a passive fetal movement sensor which is placed on the abdomen of a mother to detect the movement of a fetus in the uterus of the mother's body; a timer for outputting time information; a storage medium for storing information; and a storage control means which receives the output signal from the fetal movement sensor and stores, in the storage medium, waveform information of the output signal obtained for a period from the time when the output signal reaches a level to exceed the threshold value until the predetermined period of time elapses along with time information at the time.

The fetal movement information collecting device as claimed in claim 9 of the present invention is characterized in that the fetal movement monitoring system further comprises a mother's movement sensor to detect biological information of a mother's body, and the storage control means is configured so as to store, in the storage medium, waveform information of signals outputted from the mother's movement sensor for a period from the time when the output signal from the fetal movement sensor reaches a level to exceed the threshold value until the predetermined period of time elapses along with waveform information of the output signal of the fetal movement sensor.

The simplified fetal movement monitoring system as claimed in claim 10 of the present invention comprises: a passive fetal movement sensor which is placed on the abdomen of a mother to detect the movement of a fetus in the uterus of the mother's body; an amplifier for amplifying the output signal from the fetal movement sensor; a plurality of filters which classify fetal movement signals amplified by the amplifier according to fetal movement types and extract the fetal movement signals; a plurality of signal modulators which correspond to the filters and modulate the output signals from the filters individually to generate different output signals for display; and an indicator for clearly indicating fetal movement types on the basis of output signals for indication obtained by the modulators.

The simplified fetal movement monitoring system as claimed in claim 11 of the present invention is characterized in that the indicator is configured to indicate fetal movement types through their respective different colors, tones, melody sounds, liquid crystal screen messages, or the like.

The fetal movement monitoring system as claimed in claim 12 of the present invention comprises a fetal movement information collecting means and a simplified fetal movement monitoring system combined with each other, wherein: the fetal movement information collecting means comprises a passive fetal movement sensor which is placed on the abdomen of a mother to detect the movement of a fetus in the uterus of the mother's body, a timer for outputting time information, a storage medium for storing information, and a storage control means which receives the output signal from the fetal movement sensor and stores waveform information of the output signal obtained for a period from the time when the output signal reaches a level to exceed the threshold value until the predetermined period of time elapses along with time information corresponding to the output signal; and the simplified fetal movement monitoring system comprises an amplifier for amplifying the output signal from the fetal movement sensor, a plurality of filters which classify fetal movement signals amplified by the amplifier according to fetal movement types and extract the fetal movement signals, a plurality of signal modulators which correspond to the filters and modulate the output signals from the filters individually to generate different output signals for display, and an indicator for clearly indicating fetal movement types on the basis of output signals for indication obtained by the modulators.

The fetal movement monitoring system in combination with a simplified fetal movement monitoring system, as claimed in claim 13 of the present invention is characterized in that the fetal movement monitoring system is combined with a simplified fetal movement monitoring system comprising: an amplifier for amplifying the output signal from the fetal movement sensor; a plurality of filters which classify fetal movement signals amplified by the amplifier according to fetal movement types and extract the fetal movement signals; a plurality of signal modulators which correspond to the filters and modulate the output signals from the filters individually to generate different output signals for display; and an indicator for clearly indicating fetal movement types on the basis of output signals for indication obtained by the modulators.

The fetal movement monitoring system as claimed in claim 14 of the present invention is characterized in that the storage control means is provided with a communication means capable of communicating with an analyzing device installed at a remote location or a medical institution via a radio LAN or a communication network.

EFFECT OF THE INVENTION

The fetal movement monitoring system according to the present invention stores waveform information of the output signal from a passive fetal movement sensor obtained for a period from the time when the output signal reaches a level to exceed the threshold value until the predetermined period of time elapses along with time information, and analyzes fetal movements. Therefore, the system can store not only a fetal movement frequency, but also fetal movement information for a long time in a small capacity of storage medium. Furthermore, the system can base on waveform information for a long time to analyze in more details, allowing more correct grasp of the state of health of a fetus.

In this case, the system is configured so as to determine a fetal movement type on the basis of waveform information, allowing analysis from the fetal movement type. The system is configured to compare fetal movement occurrence patterns with fetal movement reference patterns, allowing more safety and correct determination to grasp the state of health of a fetus.

The system is configured to collect biological information about the mother's body along with fetal movement information, allowing more accurate detection of fetal movements and also grasp of information about changes in the mother's body depending on fetal movements.

As the mother's movement sensor in the system, for example, a sensor for detecting the movement, breath, and the like in the mother's body can be used to remove the influence by the movement of the mother's body from the output signal of the fetal movement sensor, allowing more accurate detection of fetal movements. Furthermore, as the mother's movement sensor, for example, a sensor for detecting brain waves and heart beats is used to give information which can be utilized to identify correlations between fetal movements and responses of the mother's body.

The fetal movement information collecting device, which has a construction from a fetal movement sensor to a storage medium of the fetal movement monitoring system, is able to store fetal movement information for a long time in a small capacity of storage medium, allowing simple collection in home of fetal movement information. The fetal movement information collecting device is used effectively in particular for a high-risk pregnant woman who is suffering from preeclampsia or the like. In addition, because a reduction in number of fetal movements is in advance acknowledged in cases of unexplained death of a fetus in the uterus, the fetal movement information collecting device can be effectively used to inform of such a state at an early stage.

The simplified fetal movement monitoring system according to the present invention, which amplifies fetal movement signals detected by a fetal movement sensor, and can extract information of waveforms having their respective different fetal movement types through a plurality of filters to display variously depending on the extracted waveforms, is useful as a simplified fetal movement monitor for home use, because the device is able to transfer fetal movement types easily and promptly to a pregnant woman and the like, can be expected to save a pregnant woman from anxiety about first childbirth and prevent the fetus from bad influence caused by the mental instability of the mother. Such a simplified fetal movement monitoring system may be combined with a fetal movement monitoring system having a storage control means for storing waveform information obtained from the fetal movement signals described above in a storage medium, allowing adequate and detail determination, diagnosis and the like as described above about waveform information stored in the storage medium.

BEST MODES FOR CARRYING OUT THE INVENTION

Next, embodiments of a fetal movement monitoring system and a fetal movement information collecting device according to the present invention will be described in detail below with reference to the accompanying drawings.

First Embodiment

A. System Configuration (1)

FIG. 1 shows a system configuration of an embodiment of a fetal movement monitoring system 20 according to the present invention. In FIG. 1, the fetal movement monitoring system 20 is composed of a fetal movement information collecting device 21 and an analyzing device 40.

The fetal movement information collecting device 21 comprises a fetal movement sensor 22, an A/D converter 23, a storage control means 24, a timer 25, and a memory 26. The analyzing device 40 comprises an analysis processing section 41 consisting of a signal waveform reproducing means 41a, a fetal movement type determining means 41b, an occurrence pattern producing means 41c, and a determining means 41d, and a display 42.

The fetal movement information collecting device 21 is compact and portable so as to allow a pregnant woman to use at home, and can be connected to/disconnected from the analyzing device 40 through an interface not shown in the figure. The fetal movement information collecting device 21 comprises a passive fetal movement sensor 22 which can be placed on a mother's abdomen with a band or the like not shown in the figures.

The fetal movement sensor 22 is an electrical capacitance acceleration detection type sensor and outputs a signal X(t) the voltage of which varies according to movements of a fetus in the uterus of the mother's body. The fetal movement sensor 22 is generally provided with an amplifier inside the sensor to use, but may be configured to have the amplifier outside the sensor to amplify the output signal from the fetal movement sensor 22.

As the electrical capacitance acceleration detection type sensor, there is suitable an acceleration detection type sensor having a weight pasted on a movable film, as described in Japanese Unexamined Patent Publication No. 2003-52690 developed by the present inventors. In other words, a common microphone type sensor for sound collection is easy to receive noise caused by cardiac sound of the pregnant woman, contact between the pregnant woman's body and any object, and rubbing sound of clothes and the like. Meanwhile, the acceleration detection type sensor having a weight pasted on a movable film, which catches the movement of the weight pasted on the movable film caused by an impact to the pregnant woman's body surface given when the fetus moves, can be used to detect only acceleration components accurately.

The output signal X(t) from the fetal movement sensor 22 is sampled on a predetermined sampling frequency fs (a frequency more than twice as much as the upper limit of the frequency range of the output signal of the sensor 22) and is converted to digital sample values X(k) by the AD converter 23. The digital sample values X(k) are then output in succession to the storage control means 24.

Sample values X(k) and time information TD outputted from the timer 25 are input to the storage control means 24 to compare with predetermined threshold values of ±R as shown in FIG. 2. When any one of the sample values falls outside the range between the threshold values of ±R, time information TD(i) at this point in time is brought into correspondence with a string of sample values [waveform information H(i)] continuously inputted during a fixed period of time Ta (e.g. 10 seconds) starting at this point in time to store in the memory 26 as the storage medium in a predetermined order of address as shown in, for example, FIG. 3.

In the memory 26, from an instant when a signal having a level of a predetermined value or more is output from the fetal movement sensor 22, waveform information H(i) of signals for a fixed period of time is stored with its time information TD (i) in succession (see FIG. 3), while waveform information of an output signal from the fetal movement sensor 22 which has a level below the predetermined value is deleted from registration. As the result, even a small capacity of the memory 26 can collect necessary waveform information caused by fetal movements over a long time.

In the memory format shown in FIG. 3, time information TD(i) is referred to as the product of the number ki of sample values outputted from the start of the measurement and a sampling period Δt, but may be indicated in hour, minute, and second data. As the memory 26, a SRAM, a rewritable flush ROM or the like, any kind of removable card memory, or an USB memory may be used. As the storage medium, a rewritable disk type one may be used.

In this embodiment, sample values X(k) obtained by A/D-converting the output signals from the fetal movement sensor 22 are compared with the threshold values of ±R. However, the output signal (analog signal) from the fetal movement sensor 22 may be compared with an analog threshold value, so that the output signals are A/D converted for a fixed period of time Ta starting at the time when one of the output signals reaches a level to exceed the threshold value to store a string of the sample values obtained by A/D conversion as waveform information in the memory 26.

Furthermore, in this embodiment, signal waveforms (a string of sample values) themselves are stored in the memory, but sample values which are able of reproducing waveforms may not be stored in the memory by way of waveforms. For example, assuming that a string of signal waveforms are composed of a series of rectangular pulses or triangular pulses as shown in FIG. 4, zero-cross times Tz (times of leading edges and trailing edges) of the pulses and a peak value Vp between the zero-cross times may be obtained to store as waveform information in the memory 26. In this case, only two pieces of information are needed per one pulse, so that waveform information for a long time can be collected in the memory 26 having a more small capacity. Time information in this case can be indicated by an elapsed time counted from the time when the signal exceeds a threshold.

On the other hand, the analyzing device 40 may comprise, for example, a personal computer and the like installed with programs for implementing means and steps described later. In other words, the analyzing device 40 is composed of an analysis processing section 41 which bases on waveform information and time information stored in the memory 26 of the fetal movement information collecting device 21 to analyze fetal movements, and a display 42. The analysis processing section 41 comprises a signal waveform reproducing means 41a for reproducing waveforms of fetal movements to indicate them on the display 42, a fetal movement type determining means 41b for determining fetal movement types, an occurrence pattern producing means 41c for producing an occurrence pattern for each of the fetal movement types, and a determining means 41d for determining the state of health of a fetus on the basis of occurrence patterns. The signal waveform reproducing means 41a reproduces a continuous waveform signal in a fixed period of time (e.g. 8 hours) on the basis of waveform information and time information stored in the memory 26 to display on the display 42.

As described above, each piece of waveform information stored in the memory 26 is obtained within a fixed period of time (about 10 seconds) stating at the time when the output signal of the fetal movement sensor 22 has a level to exceed a threshold value, and does not include signal components (noise components) for a period from the time when the fixed period of time ends until the output signal has a level to exceed the threshold again, so that the signal waveform reproducing means 41a is able to display the waveform information as shown in, for example, FIG. 5(a), assuming that waveform for this period during which waveform information has not been obtained has an amplitude of zero.

Like this, a time zone of waveforms displayed on the display 42 is decided by a doctor or the like who designates a display start times and a display period of time, or a display start time and a display end time by operating the operating section (e.g. keyboard) or the like not shown in the figures. The signal waveform reproducing means 41a extracts waveform information included in the designated time zone, and inserts waveforms having an amplitude of zero into gaps among extracted pieces of waveform information to reproduce waveforms through the whole of the designated time zone. The doctor may check these waveforms for reference of diagnosis.

Furthermore, the signal waveform reproducing means 41a has, in addition to a mode of reproducing waveforms in a designated time zone as described above, another mode of reproducing waveform information stored in the memory on a group-by-group basis to enlarge the waveform information and display the enlarged waveform information on the screen of the display 42. This mode can be implemented, for example, by two manners: the first is, as shown in FIG. 5(b), reading waveform information in the memory 26 on a group-by-group basis in order of address to display the enlarged waveform information on the full screen of the display 42; and the second is, as shown in FIG. 5(c), putting the mouse cursor K on a waveform displayed by the time zone designation mode and clicking the mouse cursor to read a group of waveform information in the position designated by the mouse and display its enlarged waveform along with the original string of waveforms. Either of the above two methods may be selected freely.

B. Analysis and Determination of Detected Fetal Movement Signals (1)

Next, analysis and determination of fetal movement signals detected by the fetal movement monitoring system 20 of this embodiment described above can be performed by the fetal movement type determining means 41b. Up to now, it has been found out that fetal movements detected by various kinds of fetal movement observations include a "kick" movement caused by sudden expansion or contraction of a hand or a foot, a "rolling" movement caused by rocking a whole body in a uterus, and a "hiccup" movement.

It has also been confirmed that the signal waveform outputted from the fetal movement sensor 22 is as follows. In the case of a "kick" movement the signal waveform occurs singly in a relatively short duration as shown in FIG. 6(a). In the case of a "rolling" movement it occurs singly in a long duration as shown in FIG. 6(b). In the case of a "hiccup" movement a vibration having a relatively short width occurs two or more times periodically as shown in FIG. 6(c).

For this reason, fetal movement types can be determined by comparing these waveform patterns with actually obtained waveform information. For example, when a waveform has a shorter duration than a fixed period of time with no periodicity acknowledged, it may be determined that a "kick" movement has occurred. When a waveform has a longer duration than a fixed period of time with no periodicity acknowledged, it may be determined that a "rolling" movement has occurred. When a waveform has a shorter duration than a fixed period of time with its periodicity acknowledged, it may be determined that a "hiccup" movement has occurred. When a waveform does not agree with any of these conditions, it is determined that an unknown type of fetal movement has occurred.

Alternatively, fetal movement types may be determined by performing spectral analysis for signals. In this case, the spectral distribution of waveform information can be obtained by performing fast Fourier transform (FET) processing for the waveform information. In other words, as expected from waveforms shown in FIGS. 6(a) to 6(c), the spectrums in the case of a "rolling" movement gather in a low frequency region as shown by the characteristic curve B in FIG. 7, spectrums in the case of a "hiccup" movement gather in a high frequency region as shown by the characteristic curve C in FIG. 7, and spectrums in the case of a "kick" movement concentrate in a frequency region between them as shown by the characteristic curve A in FIG. 7. Thus, the three fetal movement types can be easily determined by obtaining reference spectral distributions of the fetal movement types to compare the reference spectral distributions with actually obtained spectral distributions. When an actually obtained spectral distribution does not agree with any of the reference spectral distributions, it is determined that an unknown type of fetal movement has occurred.

The fetal movement type determining means 41b determines fetal movement types by any one of the methods described above on the basis of information stored in the memory 26 and signal waveforms reproduced by the signal waveform reproducing means 41a, and stores the determination results and the occurrence times in a memory not shown in the figure. Furthermore, information about fetal movement types obtained by determination of the fetal movement type determining means 41b may be identified to discriminate by adding characters or marks near displayed waveforms as shown in FIGS. 5(a) to 5(c) or coloring the displayed waveforms themselves.

Next, on the basis of fetal movement types and their occurrence times obtained as described above, the occurrence pattern producing means 41c, as shown in, for example, FIG. 8, obtains the number of occurrences per one hour for each of the fetal movement types and the number of occurrences per one hour for all of the fetal movement types (including unknown types of fetal movements), graphs them in a predetermined time zone (e.g. from 6 a.m. to 6 p.m.), and analyzes their occurrence patterns. This time zone, which depends on a collecting time zone of the fetal movement information collecting device 21, is freely decided and may be a time zone during which the pregnant woman is sleeping or a continuous time through one day.

In FIG. 8, "kick" movements have occurred most frequently between 12 o'clock and 13 o'clock, "rolling" movements have occurred on average, and "hiccup" movements have occurred about between 10 o'clock and 11 o'clock and in the evening. The number of fetal movements tends to be large in a time zone of about noon regardless of fetal movement types. For example, by such processing data for two or three days and averaging the obtained results, occurrence patterns of fetal movements in a predetermined time zone can be grasped more correctly. Occurrence patterns for each and all of fetal movement types obtained within a fixed period of time, which is assumed to continue in the same manner for several days thereafter in a healthy fetus, may be used as reference patterns.

The occurrence pattern producing means 41c stores the reference patterns in a memory not shown in the figures, and outputs occurrence patterns obtained from subsequent new waveform information to the determining means 41d. The occurrence pattern producing means 41c is configured to display the occurrence patterns obtained as described above on the screen of the display 42 through the operating section and the like.

The determining means 41d obtains correlations between occurrence patterns (which may be patterns obtained by averaging occurrence patterns for several days) inputted from the occurrence pattern producing means 41c and the reference patterns. In order to obtain correlations between the occurrence patterns, their times are shifted from each other to get a maximum correlation value. In other words, the occurrence pattern and the reference pattern, which are nearly equal to each other in whole graphical shape, can give a high correlation value to determine that the fetus is healthy, even if they have their respective time zones shifted from each other.

The correlation of occurrence patterns for every fetal movement type can be desirably obtained by selecting to compare a fetal movement type which is likely to vary remarkably with time. The occurrence patterns, which are nearly equal to each other to give a correlation value larger than a predetermined value, make it possible to determine that the fetus is healthy (growing smoothly). In contrast to this, the occurrence patterns, which are extremely different from each other in whole graphical shape, can not give any large correlation value even if they are shifted from each other in time. However, even if occurrence patterns have extremely changed and any correlation value larger than a predetermined value is not obtained, this may be transitory. When any correlation value larger than a predetermined value is not obtained like this, frequencies of all of the fetal movements are compared with last one. Only when the frequencies have surely decreased from last one, it is determined that there has been an abnormal condition (diagnosis is needed). When it is not acknowledged that the frequencies have decreased from last one, the determination may be deferred and may be carried out according to the result of the next comparison processing. Since the number of fetal movements decreases as a delivery time approaches, the frequency comparison is to be carried out in accordance with the number of weeks of the pregnancy. The determining means 41d may display these determination results on the display with, for example, characters such as "Growing Smoothly", "Determination Deferred", "Diagnosis to Need", or the like.

The analyzing device 40 which is composed of a personal computer and the like as described above is usually installed in a medical institution, and the fetal movement information collecting device 21 (or the memory 26) which has been brought by a pregnant woman at a medical examination is connected to the analyzing device 40 to allow the analyzing device 40 to perform each of the analysis processing described above. Checking the result of the analysis processing, a doctor may perform a suitable medical examination and treatment. However, an analyzing device 40 specialized so as to perform only the analysis processing may be integrated with the fetal movement information collecting device 21 to realize a portable fetal movement monitoring system. Furthermore, when a pregnant woman use such a integrated system at home, the analyzing device 40 may be designed to indicate its determination result by a luminous indicating means, a sound indicating means, a message indicating means using a liquid crystal display, or the like. According to the indicated determination result, the pregnant woman may communicate with or visit a medical institution to be examined by a doctor.

Furthermore, a system can be realized which is configured so that a communication device or an interface capable of connecting with a communication device such as a mobile phone is incorporated in the fetal movement information collecting device 21 and the analyzing device 40 to transmit information collected by the fetal movement information collecting device 21 to the analyzing device 40 of a medical institution via a communication network, so that the result of analysis of the analyzing device 40 installed in the medical institution can be returned to the fetal movement information collecting device 21 and the pregnant woman may check the returned contents.

The analyzing device 40 is configured so as to obtain reference patterns from occurrence patterns of fetal movements obtained on a single fetus to determine variations of occurrence patterns from the reference patterns, but may be configured so as to obtain reference patterns from occurrence patterns of fetal movements of two or more fetuses including the concerned fetus who have passed the almost same number of weeks of pregnancy to compare the reference patterns and occurrence patterns of individual fetus. However, there are individual differences among fetuses, so that in order to obtain reference patterns, occurrence patterns of the concerned fetus must have a high contribution.

The fetal movement information collecting device 21 is configured so as to collect waveform information and time information of the output signal from a single fetal movement sensor 21, or may be configured so as to have multiple channels for collecting waveform information of output signals from a plurality of fetal movement sensors 21. Such plurality of fetal movement sensors 21 may be attached to one pregnant woman (for example, in the case of multiple pregnancy or the like), or may be attached to a plurality of pregnant women, respectively, along with a fetal movement information collecting device in a hospital or the like, to effectively collect information about a plurality of fetuses. The former case has an advantage of being able to cancel noise signals and the like by combining signals from the fetal movement sensors with each other, changing the phases of the signals, and obtaining differences between the signals. The latter case can prevent accidents of collecting fetal movement information incorrectly and the like by bringing the fetal movement information collecting devices into correspondence with personal information such as names and dates of pregnant women (telephone numbers and/or IDs in the case of a communication network in which mobile phones are used) to collect and monitor the fetal movement information.

Second Embodiment

A. System Configuration (2)

FIG. 9 shows a system configuration of another embodiment of a fetal movement monitoring system 20' according to the present invention. For convenience of description, the same reference symbols are attached to the same components as those in the system configuration of the fetal movement monitoring system 20 of the first embodiment shown in FIG. 1, and detail description about them is omitted. In FIG. 9, the fetal movement monitoring system 20' is composed of a fetal movement information collecting device 21 and an analyzing device 40.

The fetal movement monitoring system 20' of this embodiment comprises a mother's movement sensor 28 and an A/D converter 29 in addition to the components of the fetal movement information collecting device 21 of the first embodiment. The analysis processing section 41 of the analyzing device 40 of this embodiment comprises a fetal movement information extracting means 41e in addition to the components of the analysis processing section 41 of the first embodiment. Other components of the fetal movement monitoring system 20' of this embodiment are equivalent to those of the fetal movement monitoring system 20 of the first embodiment.

The fetal movement monitoring system 20' is equipped with a mother's movement sensor (or sensors) 28 for detecting biological information about a mother's body, that is, muscle movements, breaths, heartbeats, brain waves, and the like, and an A/D converter 29 for sampling the output signal y(t) of the sensor 28, converting it to digital sample values Y(k), and outputting them to the storage control means 24.

Information from the mother's movement sensor 28 is collected along with fetal movement information from the fetal movement sensor 22, allowing not only the increased accuracy of fetal movement detection, but also grasp of information such as changes of the mother's body against fetal movements.

For example, when the fetal movement sensor 22 is susceptible to the movement of the mother's body and the like, and the output signal of the fetal movement sensor 22 includes components caused by the movement of the mother's body, a detector for detecting the movement of the mother's body and the like (which may be of the same type as the fetal movement sensor 22) is used as the mother's movement sensor 28, and thereby when storing the waveform information from the fetal movement sensor 22 in the memory 26, the storage control means 24 stores the waveform information H(i) in the memory 26 along with the waveform information M(i) of the output signal from mother's movement sensor 28 inputted in the same period which has been brought into correspondence with the waveform information H(i).

The analyzing device 40 comprises the fetal movement information extracting means 41e which excludes the influence of the movement of the mother's body included in waveform information of fetal movements to extract information which depends on only the fetal movements, and the means 41a to 41d of the analyzing device 40 analyze the information extracted by the fetal movement information extracting means 41e as described above.

B. Analysis and Determination of Detected Fetal Movement Signals and Mother's Movement Signals (2)

In the analyzing device 40 of this embodiment, when the waveform reproducing means 41a and the fetal movement type determining means 41b require waveform information from the memory 26, if the waveform information M(i) of the mother's body shown in FIG. 11(b) corresponding to the waveform information H(i) of a fetal movement stored in the memory 26 shown in FIG. 11(a) is between the predetermined threshold values of ±R', the waveform information H(i) of the fetal movement may be enlarged to output to the waveform reproducing means 41a and the fetal movement type determining means 41b as effective information.

If the waveform information M(i+1) of the mother's body corresponding to the waveform information H(i+1) of a fetal movement falls outside the range between the predetermined threshold values of ±R', the waveform information H(i+1) of the fetal movement is excluded from information given to the waveform reproducing means 41a and the fetal movement type determining means 41b assuming that any component indicating the influence of the mother's movement is included in the waveform information H(i+1).

This allows correct analysis of fetal movements to be free from waveform information which is presumed to be influenced by any movement (sporadic movement) of the mother's body. As a result, the number of fetal movements to analyze may be counted to be less than the number of actual fetal movements, but it is more safety than analyzing and counting movements of the mother's body to confuse with fetal movements.

When the output from the mother's movement sensor 28 stored along with waveform information of the output signal from the fetal movement sensor 22 falls outside the range between the threshold values of ±R', the fetal movement information extracting means 41e neglects waveform information of all of the fetal movements in the time zone. However, this does not limit the present invention. The fetal movement information extracting means 41e may be set to extract waveform information other than waveform information in a period during which it is influenced by the movement of the mother's body.

In other words, if the output from the mother's movement sensor 28 has a period during which the output falls outside the range between the threshold values of ±R' within a predetermined period of time Ta starting at the time TD(i) when the output from the fetal movement sensor 22 falls outside the range between the threshold values of ±R, the waveform information H(i)' of the fetal movement in the period (which may include short times before/after the period) is corrected to have a magnitude of zero. If the corrected waveform information H(i)' includes any portion which falls outside the range between the threshold values of ±R, the waveform information H(i)' is extracted as fetal movement information to analyze. If the corrected waveform information H(i)' includes no portion which falls outside the range between the threshold values of ±R, the waveform information H(i)' is not extracted assuming that it is ineffective information.

When the fetal movement information extracting means 41e is set like this, both information about a fetal movement which occurs prior and posterior to the movement of the mother's body within a predetermined period of time Ta, can be extracted as effective information, allowing more accurate analysis. However, waveform information corrected as described above can invite to erroneous determination of fetal movement type, so that such a fetal movement is desirably treated as an unknown type of fetal movement.

Furthermore, if a steady movement such as a breath movement of the mother's body influences the output from the fetal movement sensor 22, there is obtained in advance a relationship such as an amplitude ratio and a phase difference between the waveform of the output signal from the mother's movement sensor 28 and the waveform of the output signal from the fetal movement sensor 22 obtained when there is no fetal movement. On actual monitoring, the output signal of the mother's movement sensor 28 is multiplied by the amplitude ratio, and corrected with the phase difference, thereby to obtain signal components of the movement of the mother's body included in the output signal from the fetal movement sensor 22. The signal components are then subtracted from the waveform of the output signal from the fetal movement sensor 22 to extract waveform information depending on only fetal movements and supply it to the signal waveform reproducing means 41a and the fetal movement type determining means 41b. Since the waveform information of a fetal movement is corrected on the basis of a signal obtained by the mother's movement sensor 28 as described above, response to the magnitude and/or the changing rate of breath is possible and fetal movement information can be extracted with reliability.

Thus, if the mother's movement sensor 28 is able to detect brain waves, heartbeats, and breaths of the mother's body, they can be used as information for identifying correlations between fetal movements and response of the mother's body to the fetal movements. Although it is an important theme to know correspondences between fetal movements and response of the mother's body to the fetal movements for the mental health care of the mother and the like, much information about these correspondences has not been obtained up to now. However, if information for a long time can be collected with a small storage capacity as described above, not only fetal movement information but also biological information of brain waves and heartbeats of the mother's body can be collected, so that precious and important information which will be certainly useful for research on response of the mother's body to fetal movements, fetal movements relative to mental conditions of the mother, or the like in the future can be obtained.

Furthermore, it has been found out using the fetal movement monitoring system of this embodiment that when there is a fetal movement while the mother is sleeping, the brain wave of the sleeping mother under measurement changes to an a wave temporarily. In such a case, fetal movements can be monitored without allowing the fetal movement information extracting means 41d to function as a fetal movement monitoring system. Thus, in order to find out the relation between a fetus and a mother more deeply in the future, the fetal movement information collecting device 21 capable of collecting information for a long time and the fetal movement monitoring system 20' are extremely effective as a configuration to have the mother's movement sensor 28 as described above.

Third Embodiment

A. System Configuration (3)

FIG. 12 shows a system configuration of an embodiment of a simplified fetal movement monitoring system 30 according to the present invention. As is clear from the above description of the first embodiment, it has been found out that fetal movements detected by the fetal movement sensor 22 of the fetal movement monitoring system 30 of this embodiment include a "kick" movement caused by sudden expansion or contraction of a hand or a foot, a "rolling" movement caused by rocking a whole body in a uterus, and a "hiccup" movement. It has also been found out that a signal waveform outputted from the fetal movement sensor 22 in the case of a "kick" movement occurs singly in a relatively short duration as shown in FIG. 6(a), a signal waveform in the case of a "rolling" movement occurs singly in a long duration as shown in FIG. 6(b), and a vibration in a relatively short duration occurs two or more times periodically in the case of a "hiccup" movement.

This embodiment provides a simplified fetal movement monitoring system 30 which is designed so as to detect the characteristic of the waveform of a fetal movement signal detected by the fetal movement sensor 32, determine a fetal movement type, and display the determined fetal movement type, allowing the pregnant woman and the like to check the fetal movement type.

The simplified fetal movement monitoring system 30 of this embodiment is therefore configured, as shown in FIG. 12, so that fetal movement signals detected by a fetal movement sensor 32 are amplified by an amplifier 33, are extracted by a plurality of filters 34a, 34b to correspond to their respective fetal movement types, are modulated by their respective corresponding amplitude modulators 36a, 36b via oscillators 35a, 35b which oscillate at their respective inherent oscillating frequencies, and then are input into an indicator 38.

The indicator 38 of this embodiment may be configured so as to indicate results outputted from the amplitude modulators 36a, 36b by different color emissions, different tone or melody sounds, individual message indications on liquid crystal screens, or the like. In the example shown in the figure, there are separated into two channels various means including the filters for extracting signals in correspondence with movement types. Of course, they may be similarly into three or more channels.

Fourth Embodiment

A. System Configuration (4)

FIG. 13 shows an embodiment of a system configuration in which the simplified fetal movement monitoring system 30 described in the third embodiment is combined with the fetal movement information collecting device 21 of a fetal movement monitoring system 20 according to the present invention. For convenience of description, the same reference symbols are attached to the same components as those in the system configuration of the fetal movement monitoring system 20 of the first embodiment shown in FIG. 1, and the system configuration of the simplified fetal movement monitoring system 30 of the third embodiment shown in FIG. 12, and detail description about them is omitted. In other words, the fetal movement monitoring system of this embodiment is composed of the fetal movement information collecting device 21 and the simplified fetal movement monitoring system 30.

In this embodiment, the fetal movement sensor 22 of the fetal movement information collecting device 21 is also used as the fetal movement sensor of the simplified fetal movement monitoring system 30. This embodiment is configured, like the first embodiment, so that a communication means 50 is provided in the fetal movement information collecting device 21 to allow communication with an analyzing device 40 installed in a remote location or a medical institution via, for example, a radio LAN or a communication network, thereby to facilitate accurate and prompt determination and diagnosis related to fetal movements. Other components of this embodiment are equivalent to those of the embodiments in FIG. 1 and FIG. 12 described above.

The fetal movement monitoring system of this embodiment configured can be used simply and conveniently as the simplified fetal movement monitoring system 30 of the third embodiment as described above because both the systems use commonly the fetal movement sensor 22, and is connected to an analyzing means through the fetal movement information collecting device 21 to allow accurate and prompt determination and diagnosis related to fetal movements.

Although the preferred embodiments of the present invention have been described up to this point, the present invention is not limited to these embodiments, and various modifications in design may be possible without departing from the sprit of the present invention.

BRIEF DESCRIPTION OF THE DRAWINGS

FIG. 10 is a schematic table showing the memory format for waveform information to store in the memory of the fetal movement information collecting device in the second embodiment.

Figure 1:
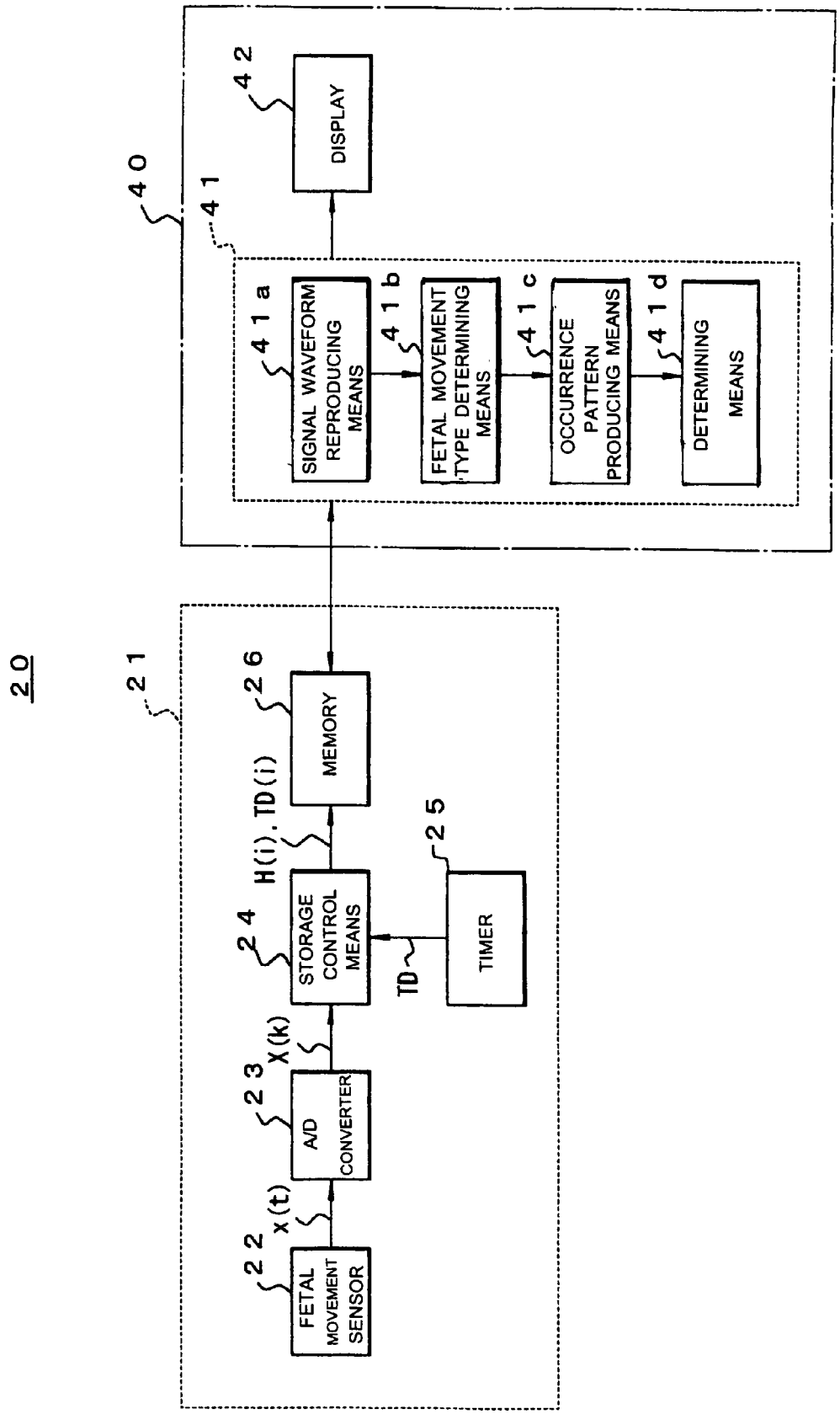
FIG. 1 is a schematic chart showing a system of a first embodiment for a fetal movement monitoring system according to the present invention.
Figure 2:
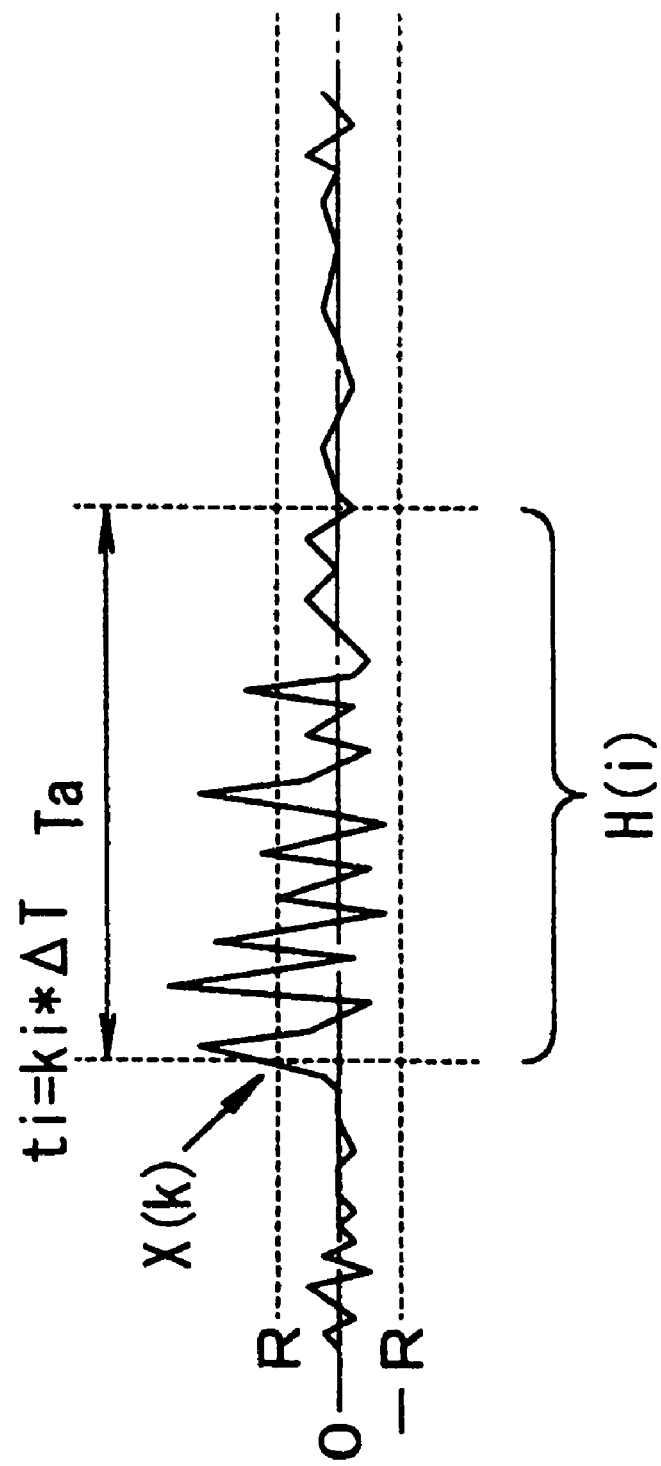
FIG. 2 is a schematic diagram showing kinetic presentation for waveform information inputted to a fetal movement sensor of a fetal movement information collecting device in the first embodiment.
Figure 3:
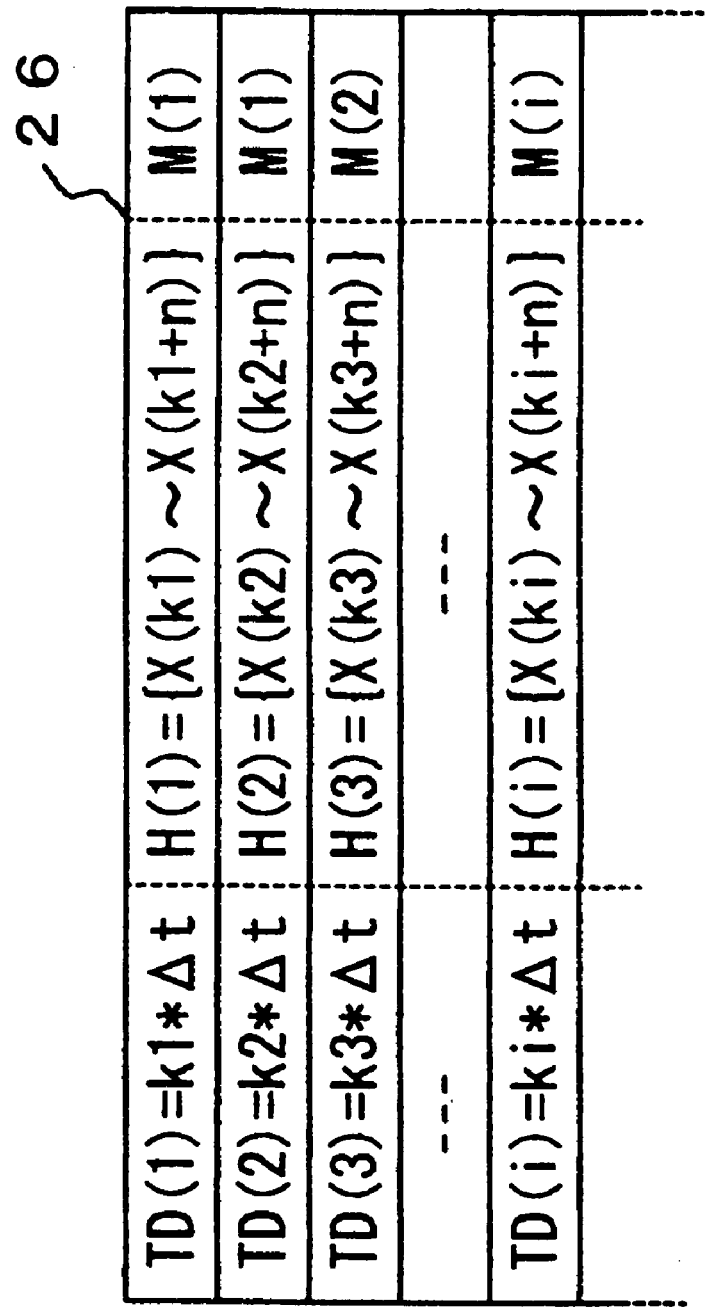
FIG. 3 is a schematic table showing a memory format for waveform information to store in a memory of the fetal movement information collecting device in the first embodiment.
Figure 4:
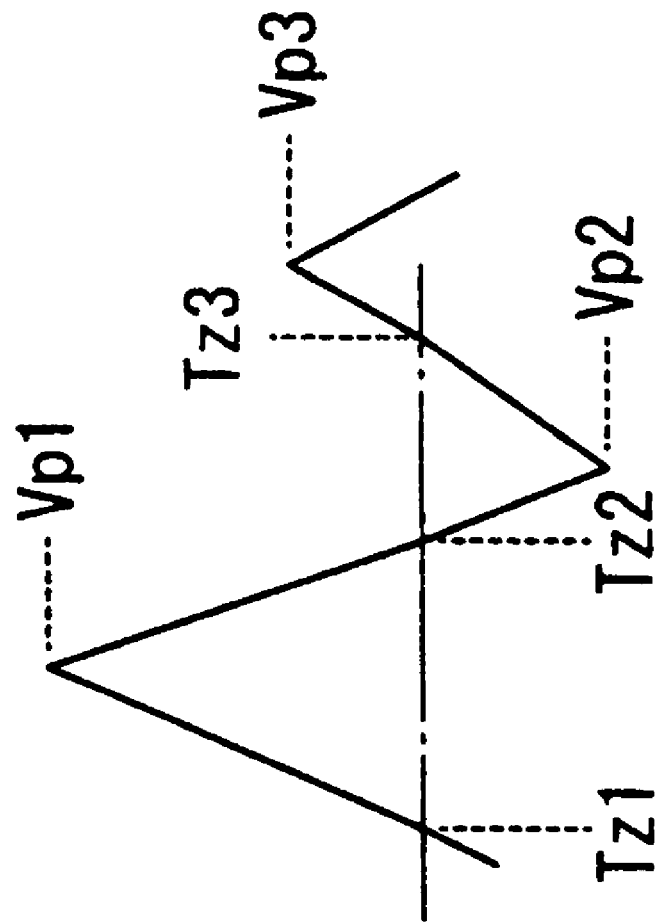
FIG. 4 is a schematic diagram showing another presentation for waveform information stored in the memory of the fetal movement information collecting device of the first embodiment.
Figure 5:
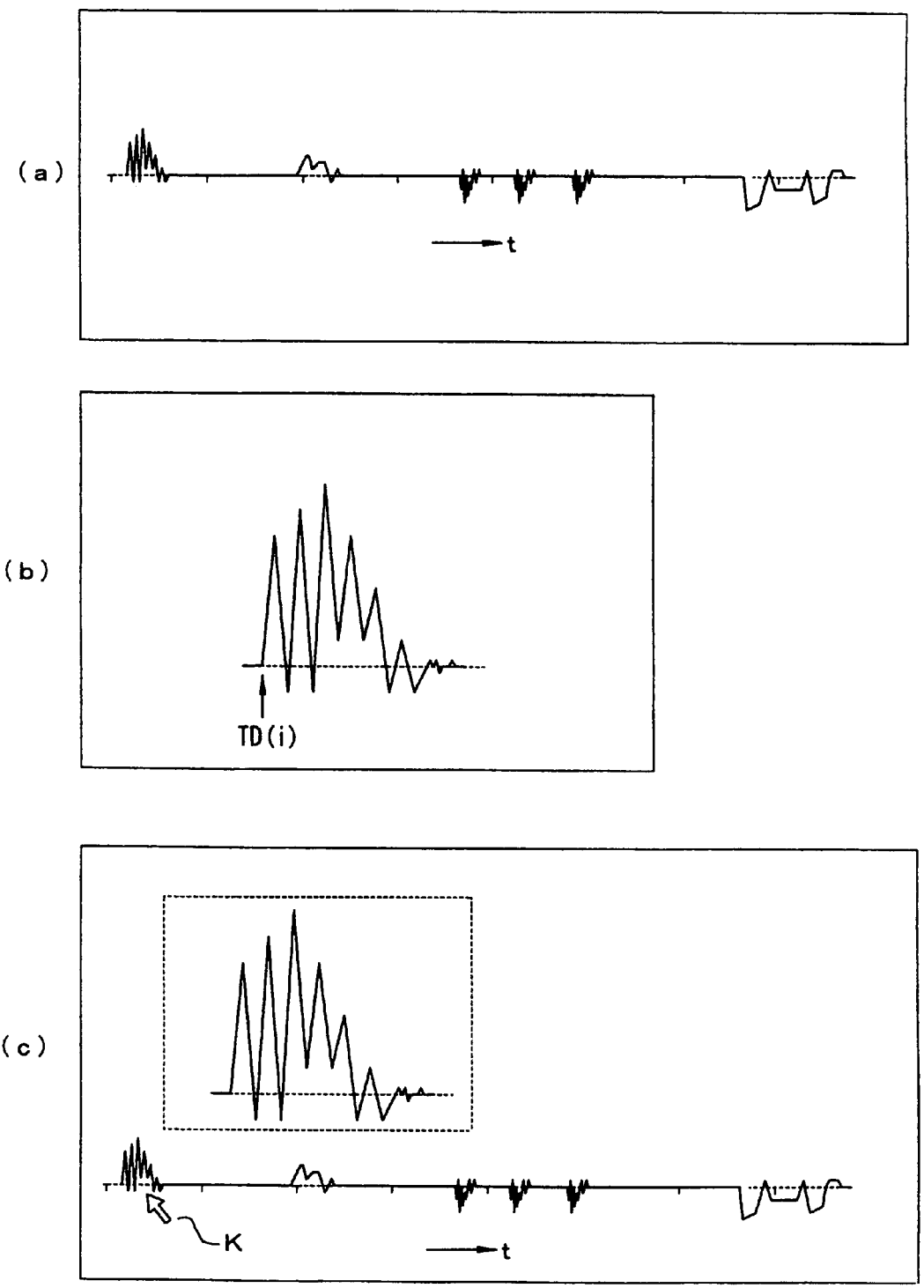
FIG. 5 is a schematic diagram showing waveform information reproduced by a signal waveform reproducing means of an analyzing device of the first embodiment; (a) a schematic diagram showing waveform information in a fixed period of time, (b) a schematic diagram showing an enlarged main part of waveform information shown in (a), and (c) a schematic diagram showing waveform information together with the enlarged main part shown in (a).
Figure 6:
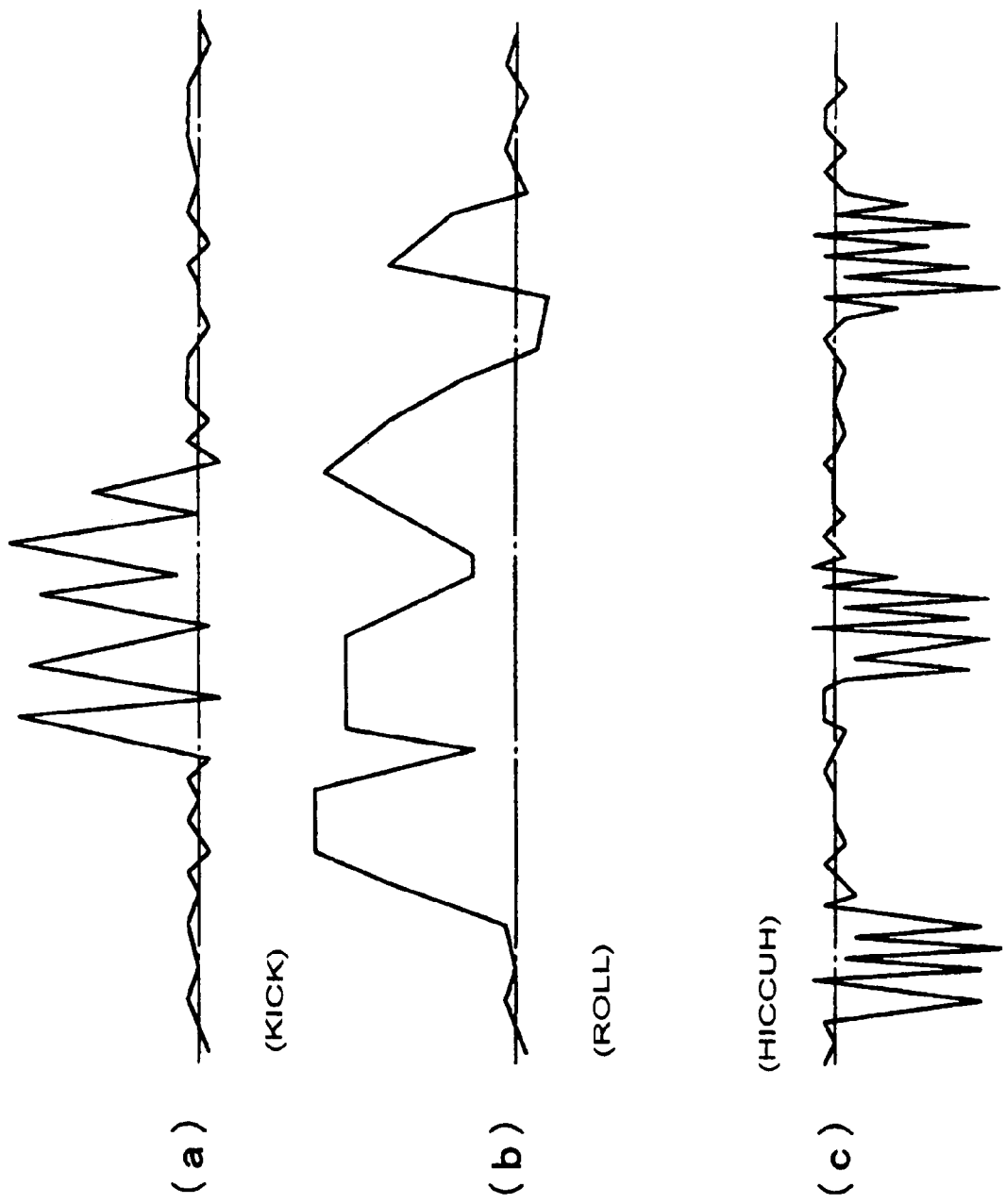
FIG. 6 is a schematic diagram showing waveform information with respect to fetal movement types reproduced by the signal waveform reproducing means of the analyzing device in the first embodiment; (a) is a waveform chart showing a "kick" movement as a fetal movement type, (b) is a waveform chart showing a "rolling" movement as a fetal movement type, and (c) is a waveform chart showing a "hiccup" movement as a fetal movement type.
Figure 7:
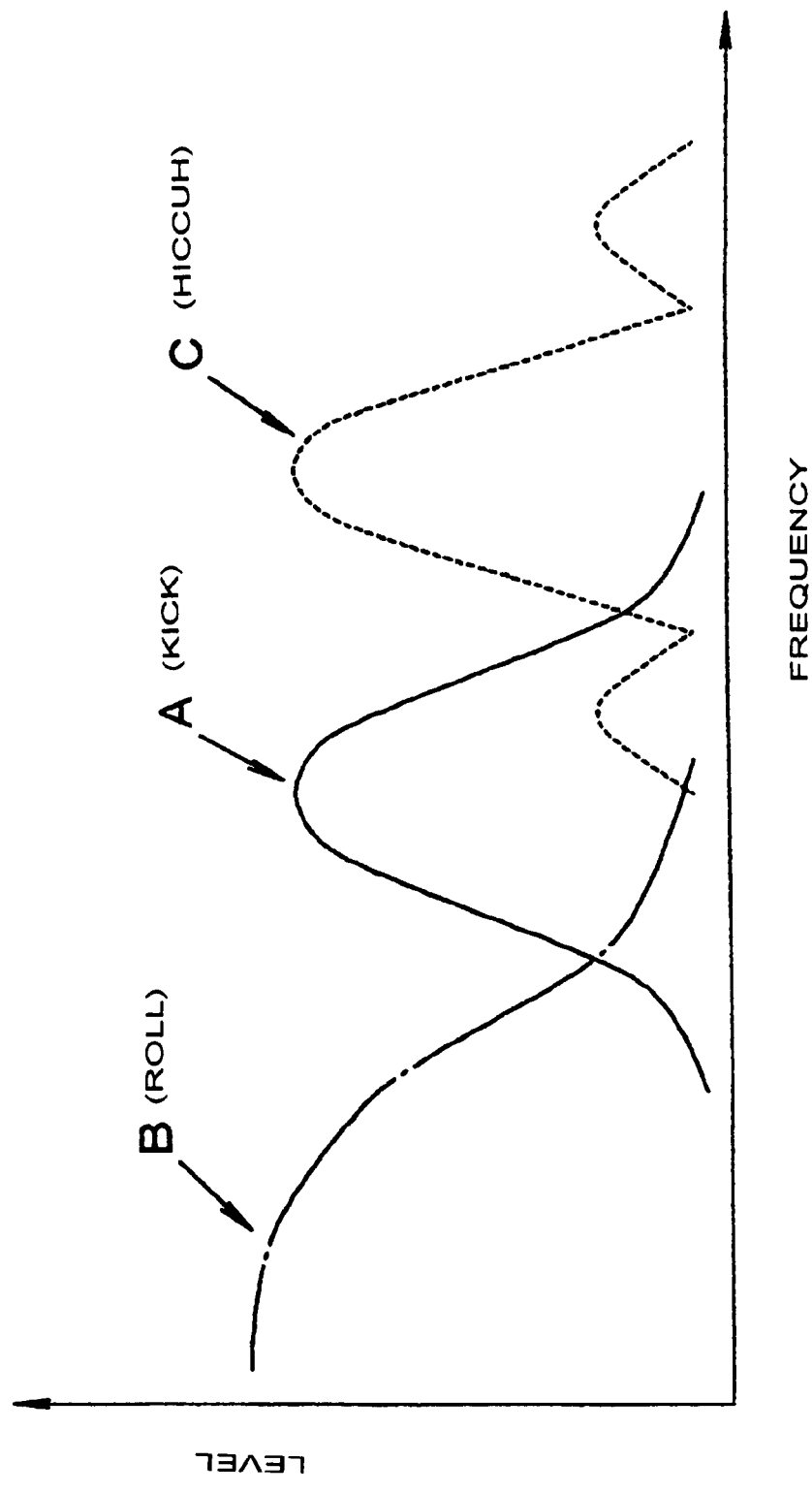
FIG. 7 is a characteristic curve showing a spectral distribution as another presentation of waveform information with respect to fetal movement types reproduced by the signal waveform reproducing means of the analyzing device in the first embodiment.
Figure 8:
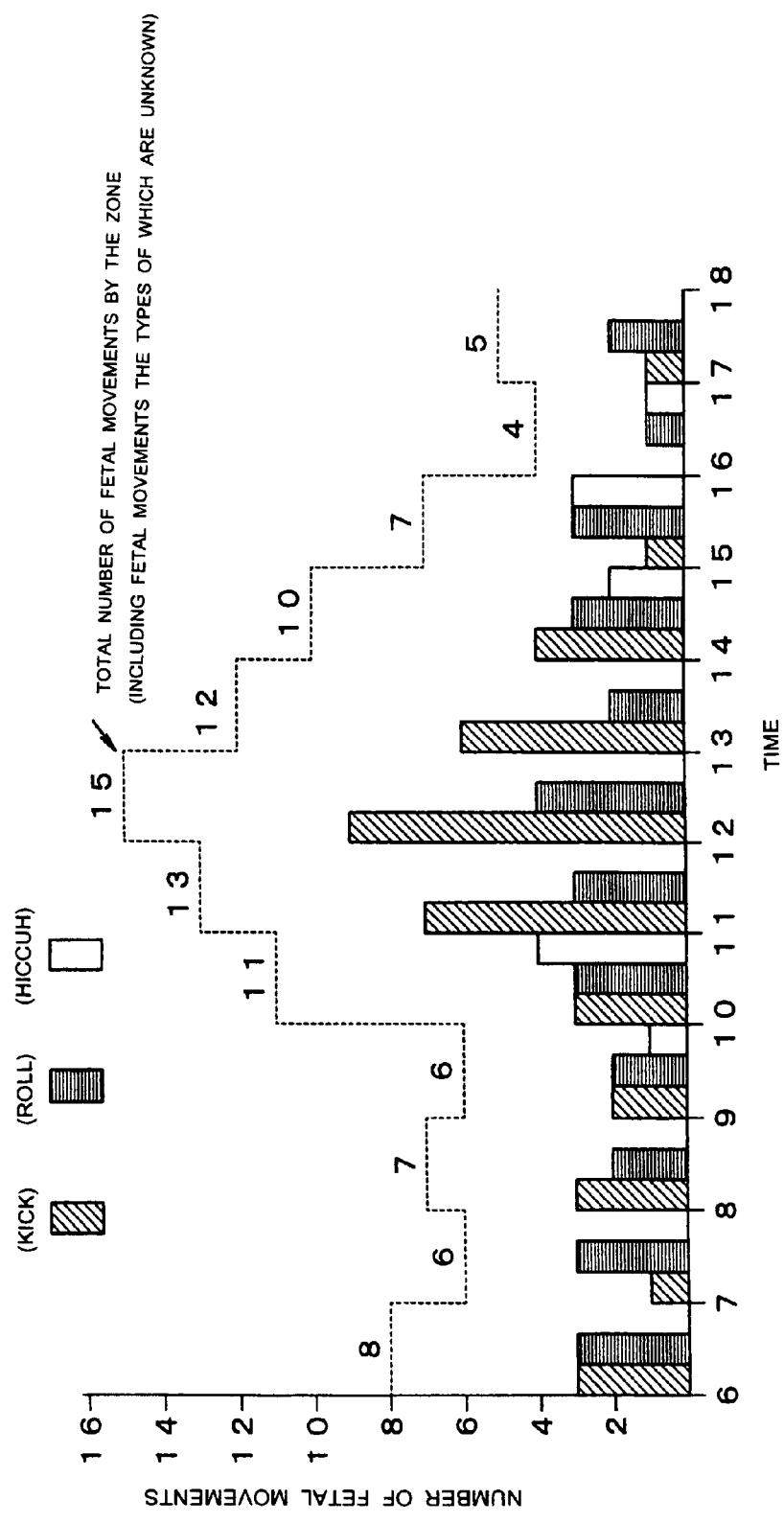
FIG. 8 is an analytical graph showing fetal movement patterns reproduced by an occurrence pattern producing means of the analyzing device in the first embodiment.
Figure 9:
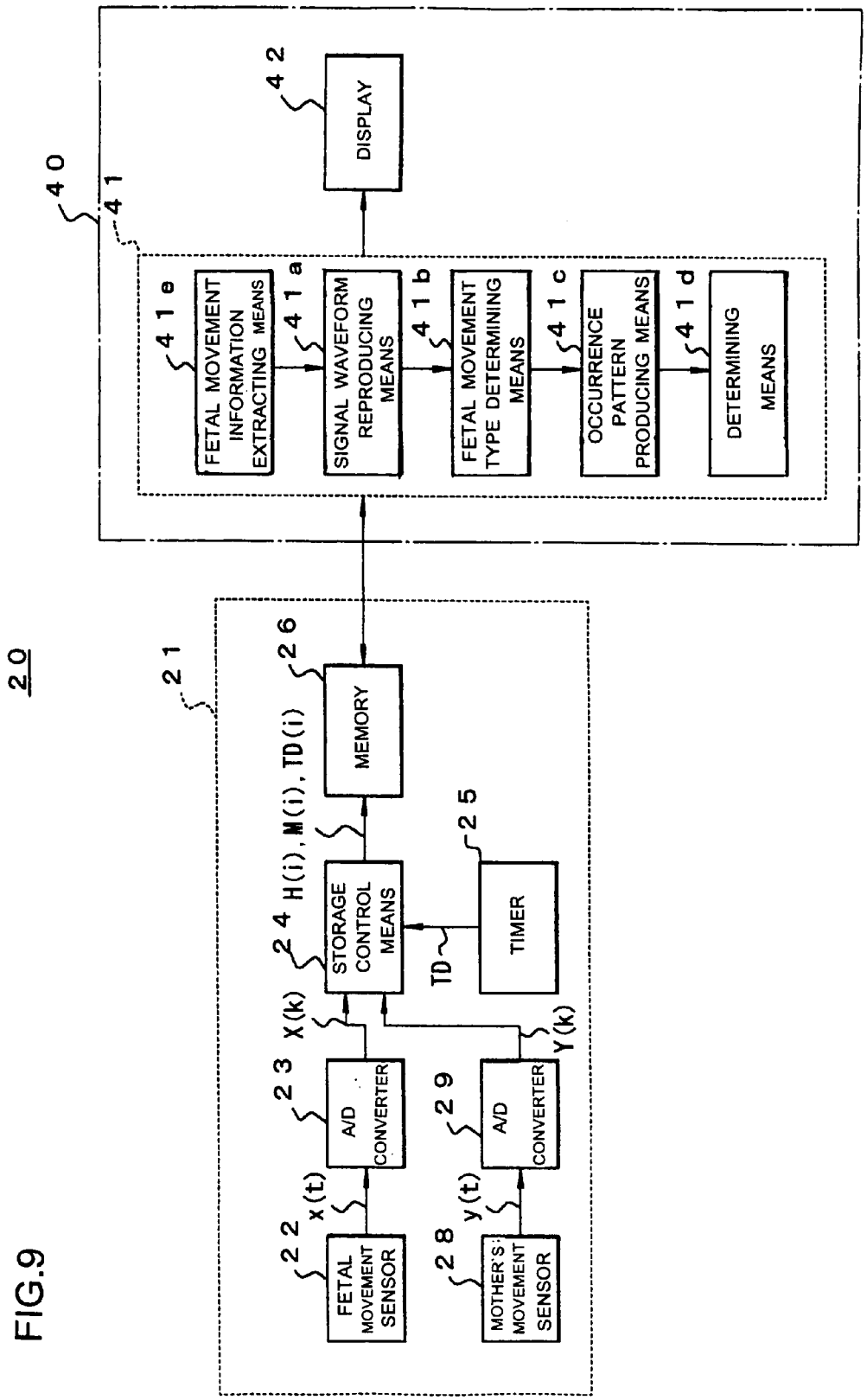
FIG. 9 is a schematic chart showing a system of a second embodiment for the fetal movement monitoring system according to the present invention.
Figure 11:
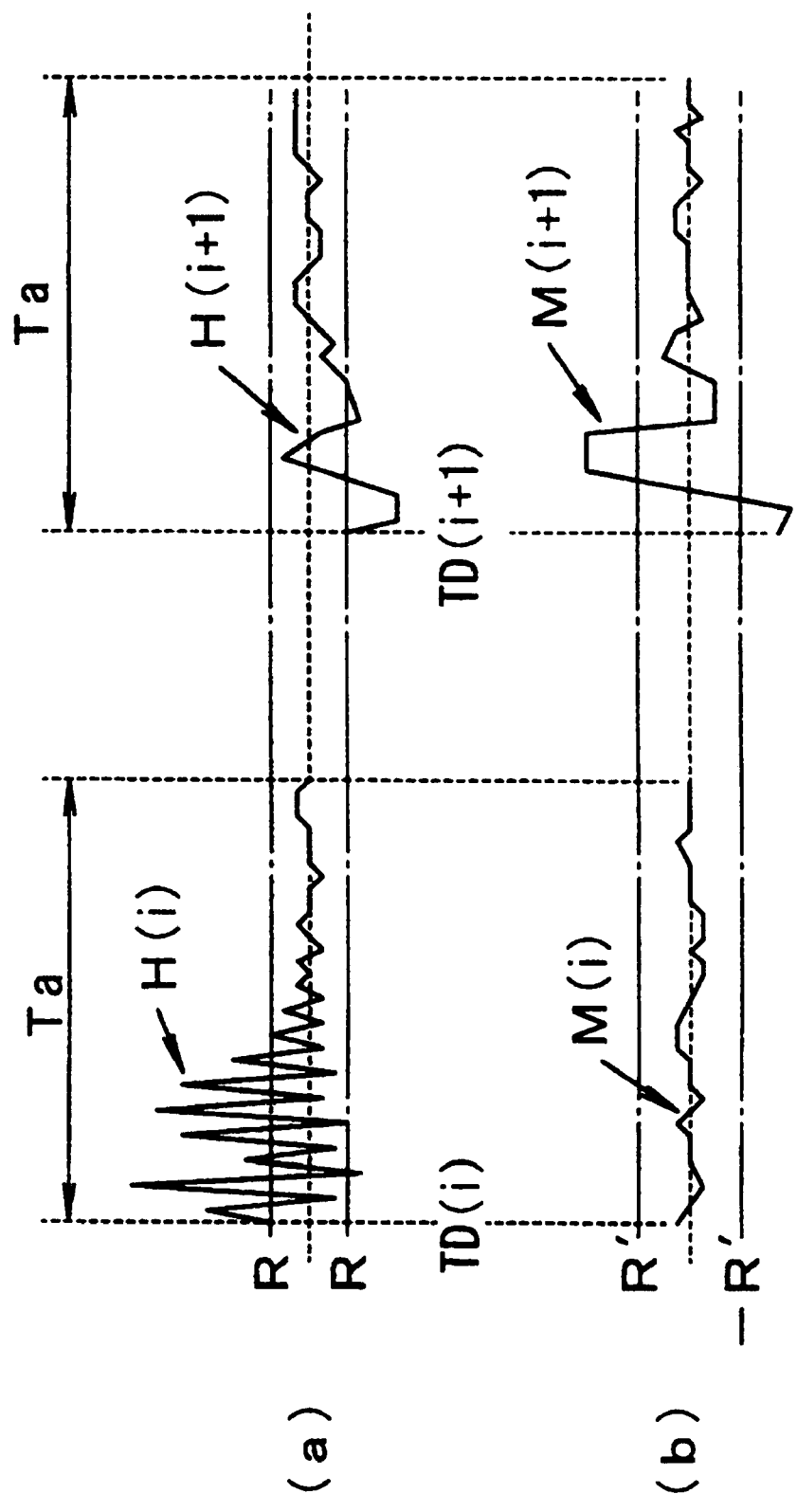
FIG. 11 shows relations between the output from the fetal movement sensor and the output from the mother's movement sensor of the analyzing device in the second embodiment; (a) a schematic diagram showing waveform information of fetal movements, and (b) a schematic diagram showing waveform information of the mother's body.
Figure 12:
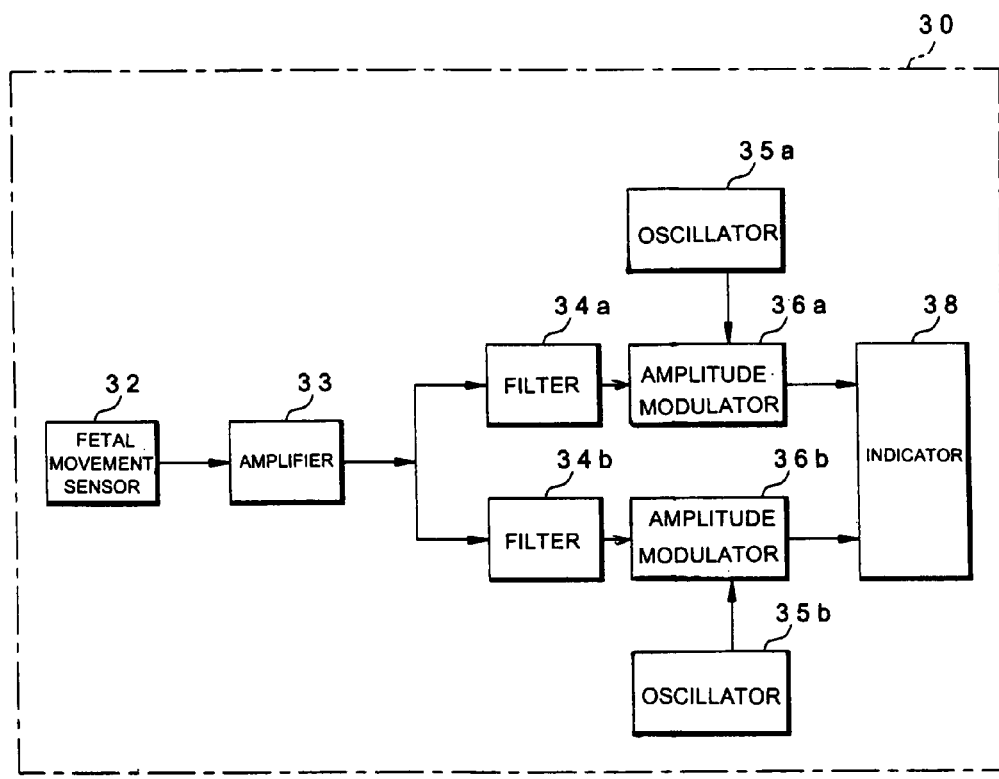
FIG. 12 is a schematic chart showing a system of a third embodiment for the fetal movement monitoring system according to the present invention.
Figure 13:
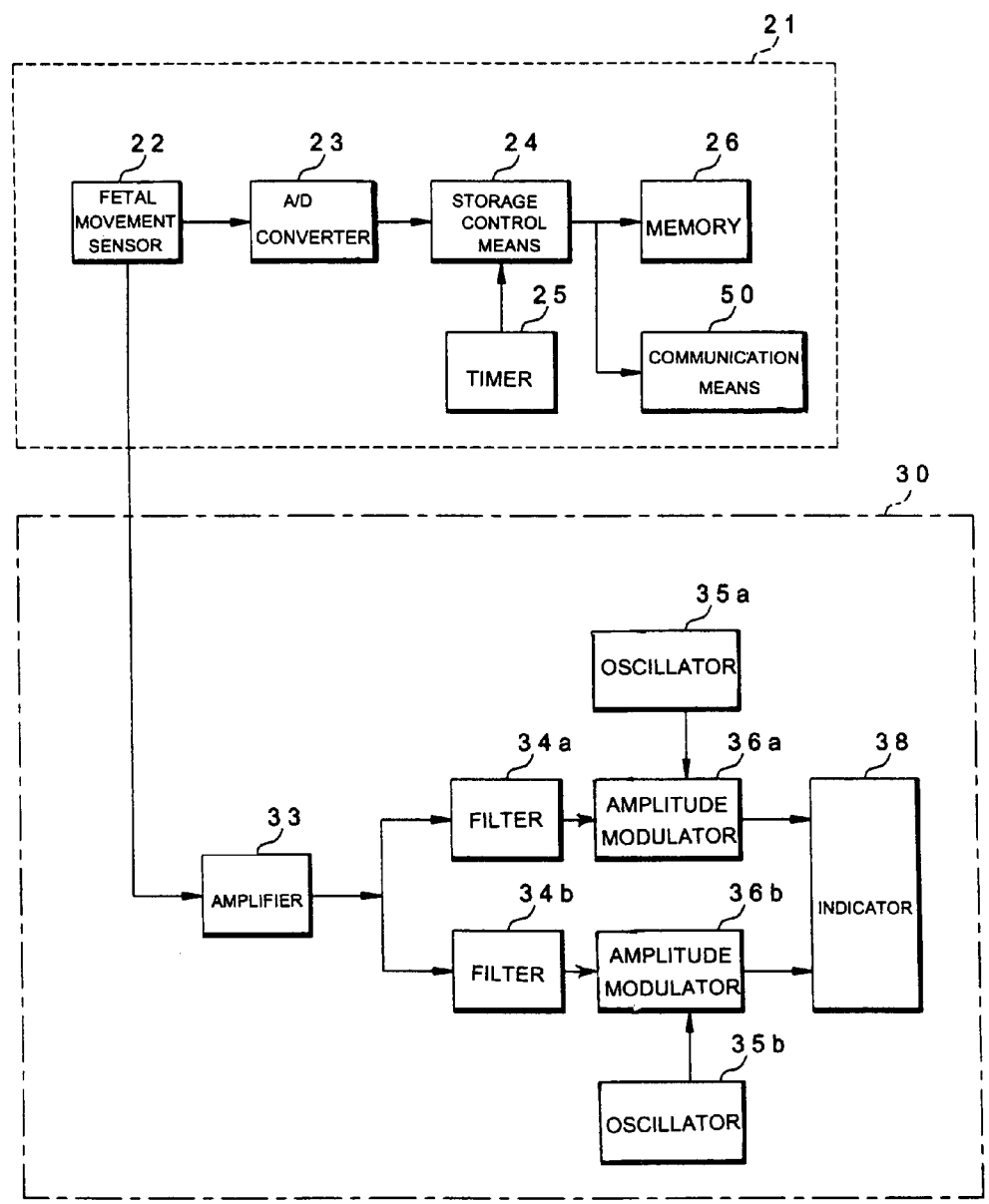
FIG. 13 is a schematic chart showing a system of a fourth embodiment for the fetal movement monitoring system according to the present invention.

DESCRIPTION OF THE REFERENCE SYMBOLS 20, 20': fetal movement monitoring system
21: fetal movement information collecting device
22: fetal movement sensor
23: A/D converter
24: storage control means
25: timer
26: memory
28: mother's movement sensor
29: A/D converter
30: simplified fetal movement monitoring system
32: fetal movement sensor
33: amplifier
34a, 34b: filter
35a, 35b: oscillator
36a, 36b: amplitude modulator
38: indicator
40: analyzing device
41: analysis processing section
41a: signal waveform reproducing means
41b: fetal movement type determining means
41c: occurrence pattern producing means
41d: determining means
41e: fetal movement information extracting means
42: display
H(i): waveform information of a fetal movement
M(i): waveform information of the mother's body movement

The invention claimed is:

1. A fetal movement monitoring system comprising an analyzing device which reads information from a memory and determines if a fetus is growing smoothly, said memory being stored with:
fetal movement waveform information that corresponds to an output signal from a passive fetal movement sensor which is placed on abdomen of a mother and detects movement of a fetus in a mother's body;
time information that corresponds to said output signal from said passive fetal movement sensor; and
waveform information on mother's movement that corresponds to output signals of a mother's movement sensor which is placed on the mother's body and detects mother's movement;
wherein said analyzing device comprises:
a fetal movement information extracting means
which, if waveform information of mother's body stored correspondingly to waveform information of fetal movement stored in said memory is less predetermined threshold values, extracts and outputs the waveform information of fetal movement as effective output signal, and
which, if waveform information of mother's body exceeds the predetermined threshold values, prevents waveform information of fetal movement from being outputted from said memory by way of assuming that any component indicating influence of the mother's movement is included in the waveform information of fetal movement;
a signal waveform reproducing means which
obtains, based on a relationship between waveform of output signal from said fetal movement sensor and waveform of output signal from the mother's movement sensor both obtained when there is no fetal movement, signal component of movement of mother's body included in the waveform of output signal from said fetal movement sensor,
subtracts the signal component of movement of mother's body from the effective waveform of output signal, and
extracts and outputs waveform information, which depends only on fetal movements, as an effective fetal movement information;
a fetal movement type determining means which
displays, on a display, the effective fetal movement information and the time information, and
determines fetal movement types based on signal waveforms reproduced by said signal waveform reproducing means;
an occurrence pattern producing means which,
obtains, based on fetal movement type information obtained by said fetal movement type determining means and on the effective fetal movement information, number of occurrences per unit time of the fetal movement, and
obtains effective fetal movement occurrence patterns comprising fetal movement types during predetermined number of weeks of pregnancy and the number occurrence of fetal movement; and
a determining means which
performs correlation processing for obtaining correlations between reference fetal movement patterns, which are obtained from data of a plurality of fetuses for every week of pregnancy with respect to types of and number of occurrence of the fetal movement and stored in advance, and said effective fetal movement occurrence pattern of predetermined number of weeks of pregnancy, which is obtained by said fetal movement type determining means, and
determines state of health of the fetus based on obtained correlation values.

* * * * *